United States Patent
Swamy et al.

(10) Patent No.: US 8,831,311 B2
(45) Date of Patent: Sep. 9, 2014

(54) METHODS AND SYSTEMS FOR AUTOMATED SOFT TISSUE SEGMENTATION, CIRCUMFERENCE ESTIMATION AND PLANE GUIDANCE IN FETAL ABDOMINAL ULTRASOUND IMAGES

(71) Applicant: General Electric Company, Schenectady, NY (US)

(72) Inventors: Gokul Swamy, Bangalore (IN); Rui Li, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 98 days.

(21) Appl. No.: 13/731,140

(22) Filed: Dec. 31, 2012

(65) Prior Publication Data

US 2014/0185895 A1  Jul. 3, 2014

(51) Int. Cl.
*G06T 7/00* (2006.01)
*G06K 9/46* (2006.01)

(52) U.S. Cl.
CPC ........................................ *G06K 9/46* (2013.01)
USPC ........................................ 382/128; 600/443

(58) Field of Classification Search
CPC ............... G06T 7/0012; G06T 7/0014; G06T 2207/10132; G06T 2207/30044; G06K 2209/05; G06K 2209/051; A61B 8/08; A61B 8/0833; A61B 8/085; A61B 8/0866; A61B 8/52; A61B 8/5233
USPC ........... 382/100, 128, 173, 286; 600/437, 443
See application file for complete search history.

(56) References Cited

U.S. PATENT DOCUMENTS

| | | | |
|---|---|---|---|
| 5,588,435 A | 12/1996 | Weng et al. | 128/660.07 |
| 5,838,592 A | 11/1998 | Spratt | 364/560 |
| 7,783,095 B2 | 8/2010 | Carneiro et al. | 382/128 |
| 8,083,678 B2 | 12/2011 | Abuhamad | 600/443 |
| 2008/0240532 A1 | 10/2008 | Carneiro et al. | 382/131 |

(Continued)

FOREIGN PATENT DOCUMENTS

CN  102151149 A  8/2011  ............... A61B 8/00

OTHER PUBLICATIONS

Carneiro et al., "Automatic Fetal Measurements in Ultrasound Using Constrained Probabilistic Boosting Tree", Medical Image Computing and Computer-Assisted Intervention—MICCAI, vol. 4792, pp. 571-579, 2007.

(Continued)

*Primary Examiner* — Andrew W Johns
(74) *Attorney, Agent, or Firm* — Eileen B. Gallagher (57) ABSTRACT

A computer-implemented method for analyzing a fetal ultrasound image includes accessing a first statistical model calculated from training data representing shapes of conforming fetal abdominal tissue exemplars and accessing image data representing a scan plane in an ultrasound image. The method further includes identifying a region of interest including an abdomen in the scan plane using the first statistical model, accessing a second statistical model calculated from training data representing shapes of conforming fetal anatomical structure exemplars, determining whether one or more anatomical structures are present within the region of interest using the second statistical model, and assigning a rating to the scan plane based on the presence of the one or more anatomical structures in the region of interest. The anatomical structures may include a stomach and/or a portal vein. The method may include calculating an estimated circumference of the abdomen.

27 Claims, 5 Drawing Sheets

(56) References Cited

U.S. PATENT DOCUMENTS

| | | | |
|---|---|---|---|
| 2008/0306385 A1 | 12/2008 | Jago et al. | 600/443 |
| 2010/0217123 A1* | 8/2010 | Eran et al. | 600/437 |
| 2011/0125016 A1 | 5/2011 | Lazebnik et al. | 600/443 |

OTHER PUBLICATIONS

Carneiro et al., "Detection and Measurement of Fetal Anatomies from Ultrasound Images using a Constrained Probabilistic Boosting Tree", IEEE Transactions on Medical Imaging, vol. 27, Issue 9, pp. 1342-1355, Sep. 2008.

Carneiro et al., "Knowledge-based Automated Fetal Biometrics", Siemens, Sep. 2008, Whitepaper.

Nguyen et al., "Surface Extraction Using SVM-Based Texture Classification for 3D Fetal Ultrasound Imaging", First International Conference on Communications and Electronics (ICCE), pp. 285-290, Oct. 10-11, 2006.

Odegard et al., "Automatic diagnosis of ultrasound images using standard view planes of fetal anatomy", NTNU (Norwegian University of Science and Technology), 2006, MS Thesis (Dept of computer science).

Rahmatullah et al.,"Automated Selection of Standardized Planes from Ultrasound Volume", Proceedings of the Second international conference on Machine learning in medical imaging (MLMI'11), vol. 7009, pp. 35-42, 2011.

Rahmatullah et al., "Quality Control of Fetal Ultrasound Images: Detection of Abdomen Anatomical Landmarks Using Adaboost", IEEE International Symposium on Biomedical Imaging: From Nano to Macro, pp. 6-9, Mar. 30, 2011- Apr. 2, 2011.

Yu et al., "Fetal Abdominal Contour Extraction and Measurement in Ultrasound Images", Ultrasound in Medicine & Biology, vol. 34, Issue 2, pp. 169-182, Feb. 2008.

\* cited by examiner

METHODS AND SYSTEMS FOR AUTOMATED SOFT TISSUE SEGMENTATION, CIRCUMFERENCE ESTIMATION AND PLANE GUIDANCE IN FETAL ABDOMINAL ULTRASOUND IMAGES

FIELD

This disclosure relates generally to the ultrasound image analysis, and more particularly, to systems and methods for automated soft tissue segmentation, circumference estimation and/or scan-plane guidance in fetal abdominal ultrasound images.

BACKGROUND

Fetal abdomen scanning is routinely performed in obstetric practice. For example, fetal anatomic measurements pertaining to the femur length, cranial circumference and abdominal circumference are routinely performed during obstetric ultrasound scanning, and can be used as indicators of gestational age and fetal growth pattern.

In performing these measurements it is important that the fetal anatomy is imaged in the correct scan plane and that measurements are made consistent with clinical guidelines to ensure reproducibility of the measurements. There can be considerable variability in the maternal abdominal lining, fetal size and presentation with gestational age and movement that translates into variability in the texture, scale, intensity, and noise, in addition to the presence of artifacts in ultrasound images. Therefore, while obtaining the correct scan plane and making a manual measurement with a mouse-like caliper provided in an ultrasound scanner can be a matter of routine for an expert sonographer, making such a measurement may be confounding for a novice user or mid-wife. This is particularly true of soft tissue imaging, since the impedance mismatch at a soft tissue boundary is much less pronounced than at boundaries of bony structures, and therefore soft-tissue appearance can be obfuscated by proximal anatomies and speckle noise. Soft tissue is also prone to artifacts arising from its inherent deformability. Conventional techniques for mitigating some of these issues can inadequately address the problem of guiding the clinician towards a correct scan plane for making reproducible measurements.

SUMMARY

According to an embodiment, a computer includes a processor and a memory operatively coupled to the processor. A computer-implemented method for analyzing a fetal ultrasound image includes accessing, in the memory, a first statistical model calculated from training data representing shapes of conforming fetal abdominal tissue exemplars and accessing, in the memory, image data representing a scan plane in an ultrasound image. The method further includes identifying, by the processor, a region of interest including an abdomen in the scan plane using the first statistical model, accessing, in the memory, a second statistical model calculated from training data representing shapes of conforming fetal anatomical structure exemplars, determining, by the processor, whether one or more anatomical structures are present within the region of interest using the second statistical model, and assigning, by the processor, a rating to the scan plane based on the presence of the one or more anatomical structures in the region of interest.

In some embodiments, the anatomical structures may include a stomach and/or a portal vein. In some embodiments, the method may further include assigning the rating to be good, if both the stomach and the portal vein are present in the scan plane; acceptable, if either the stomach or the portal vein is present in the scan plane; or bad, otherwise. In some embodiments, the method may further include displaying, by the processor via an operator display operatively coupled to the processor, the rating and the region of interest.

In some embodiments, the method may further include calculating, by the processor, an estimated circumference of the abdomen. In some embodiments, the method may further include enhancing, by the processor, the ultrasound image using a filter so as to increase a contrast between the abdomen and other anatomical structures present in the scan plane. In some embodiments, the step of calculating the estimated circumference may include generating, by the processor, a contour of the abdomen, and measuring a length of the contour. The contour may be coincident to a boundary between the abdomen and the other anatomical structures present in the scan plane. In some embodiments, the method may further include removing, by the processor, noise artifacts adjacent to the contour. In some embodiments, the method may further include fitting a predefined geometric shape to the contour.

According to an embodiment, a non-transitory computer-readable medium has stored thereon computer-executable instructions that when executed by a computer cause the computer to access a first statistical model calculated from training data representing shapes of conforming fetal abdominal tissue exemplars, access image data representing a scan plane in an ultrasound image, identify a region of interest including an abdomen in the scan plane using the first statistical model, access a second statistical model calculated from training data representing shapes of conforming fetal anatomical structure exemplars, determine whether one or more anatomical structures are present within the region of interest using the second statistical model, and assign a rating to the scan plane based on the presence of the one or more anatomical structures in the region of interest.

In some embodiments, the anatomical structures may include a stomach and/or a portal vein. In some embodiments, the computer-readable medium may further include computer-executable instructions that when executed by the computer cause the computer to assign the rating to be good, if both the stomach and the portal vein are present in the scan plane; acceptable, if either the stomach or the portal vein is present in the scan plane; or bad, otherwise. In some embodiments, the computer-readable medium may further include computer-executable instructions that when executed by the computer cause the computer to display, via an operator display, the rating and the region of interest.

In some embodiments, the computer-readable medium may further include computer-executable instructions that when executed by the computer cause the computer to calculate an estimated circumference of the abdomen. In some embodiments, the computer-readable medium may further include computer-executable instructions that when executed by the computer cause the computer to enhance the ultrasound image using a filter so as to increase a contrast between the abdomen and other anatomical structures present in the scan plane. In some embodiments, the computer-readable medium may further include computer-executable instructions that when executed by the computer cause the computer to generate a contour of the abdomen and measure a length of the contour. The contour may be coincident to a boundary between the abdomen and the other anatomical structures in the scan plane. In some embodiments, the computer-readable medium may further include computer-executable instructions that when executed by the computer cause the computer to remove noise artifacts adjacent to the contour. In some embodiments, the computer-readable medium may further include computer-executable instructions that when executed by the computer cause the computer to fit a predefined geometric shape to the contour.

In an embodiment, a system for analyzing a fetal abdominal ultrasound image includes a processor, an input operatively coupled to the processor and configured to receive image data representing a scan plane in an ultrasound image, and a memory operatively coupled to the processor. The memory includes computer-executable instructions that when executed by the processor cause the processor to access a first statistical model calculated from training data representing shapes of conforming fetal abdominal tissue exemplars, access the image data, identify a region of interest including an abdomen in the scan plane using the first statistical model, access a second statistical model calculated from training data representing shapes of conforming fetal anatomical structure exemplars, determine whether one or more anatomical structures are present within the region of interest using the second statistical model, and assign a rating to the scan plane based on the presence of the one or more anatomical structures in the region of interest.

In some embodiments, the anatomical structures may include a stomach and/or a portal vein. In some embodiments, the memory may further include computer-executable instructions that when executed by the processor cause the processor to assign the rating to be good, if both the stomach and the portal vein are present in the scan plane; acceptable, if either the stomach or the portal vein is present in the scan plane; or bad, otherwise. In some embodiments, the memory may further include computer-executable instructions that when executed by the processor cause the processor to display, via an operator display, the rating and the region of interest.

In some embodiments, the memory may further include computer-executable instructions that when executed by the processor cause the processor to calculate an estimated circumference of the abdomen. In some embodiments, the memory may further include computer-executable instructions that when executed by the processor cause the processor to enhance the ultrasound image using a filter so as to increase a contrast between the abdomen and other anatomical structures present in the scan plane. In some embodiments, the memory may further include computer-executable instructions that when executed by the processor cause the processor to generate a contour of the abdomen and measure a length of the contour. The contour may be coincident to a boundary between the abdomen and the other anatomical structures in the scan plane. In some embodiments, the memory may further include computer-executable instructions that when executed by the processor cause the processor to remove noise artifacts adjacent to the contour. In some embodiments, the memory may further include computer-executable instructions that when executed by the processor cause the processor to fit a predefined geometric shape to the contour.

BRIEF DESCRIPTION OF THE DRAWINGS

Features and aspects of embodiments are described below with reference to the accompanying drawings, in which elements are not necessarily depicted to scale.

DETAILED DESCRIPTION

Embodiments of the present disclosure are directed to systems and methods for automated scan plane guidance, soft-tissue segmentation and/or fetal abdominal measurement in ultrasound images. Soft tissue contrast may be limited in ultrasound images because of a relatively small impedance mismatch between the soft tissue and surrounding regions. During obstetric ultrasound scanning it can be difficult to manually image anatomically correct scan planes when the object of interest (e.g., a fetal abdomen) is primarily soft tissue. Exemplary embodiments advantageously automate the process of guiding the clinician toward a correct scan plane.

According to some embodiments, a computer-implemented image processing method, which may be performed in real-time (e.g., contemporaneously), provides guidance to a user during the scan process by rating the correctness of the imaged scan plane. In some embodiments, a computer-implemented image processing method for soft tissue segmentation segments the soft-tissue features in an ultrasound image based at least in part on the coherent nature of biological tissue. Such scan plane guidance and segmentation can enable a user to perform ultrasound scans that improve the accuracy of the diagnostic outcome by reducing or eliminating user-induced variability and introduce or improve the reproducibility of the fetal abdomen measurements. Although some embodiments disclosed herein are directed to fetal abdomen ultrasound imaging, it will be understood that some other embodiments can be used for guidance and automated measurement of other anatomies (fetal and non-fetal), such as cardiac, renal, etc. The system 100 may be operatively coupled to a storage device 140 for storing and/or retrieving, for example, data representing image data, training data, statistical model data and/or computer-executable instructions.

Figure 1:
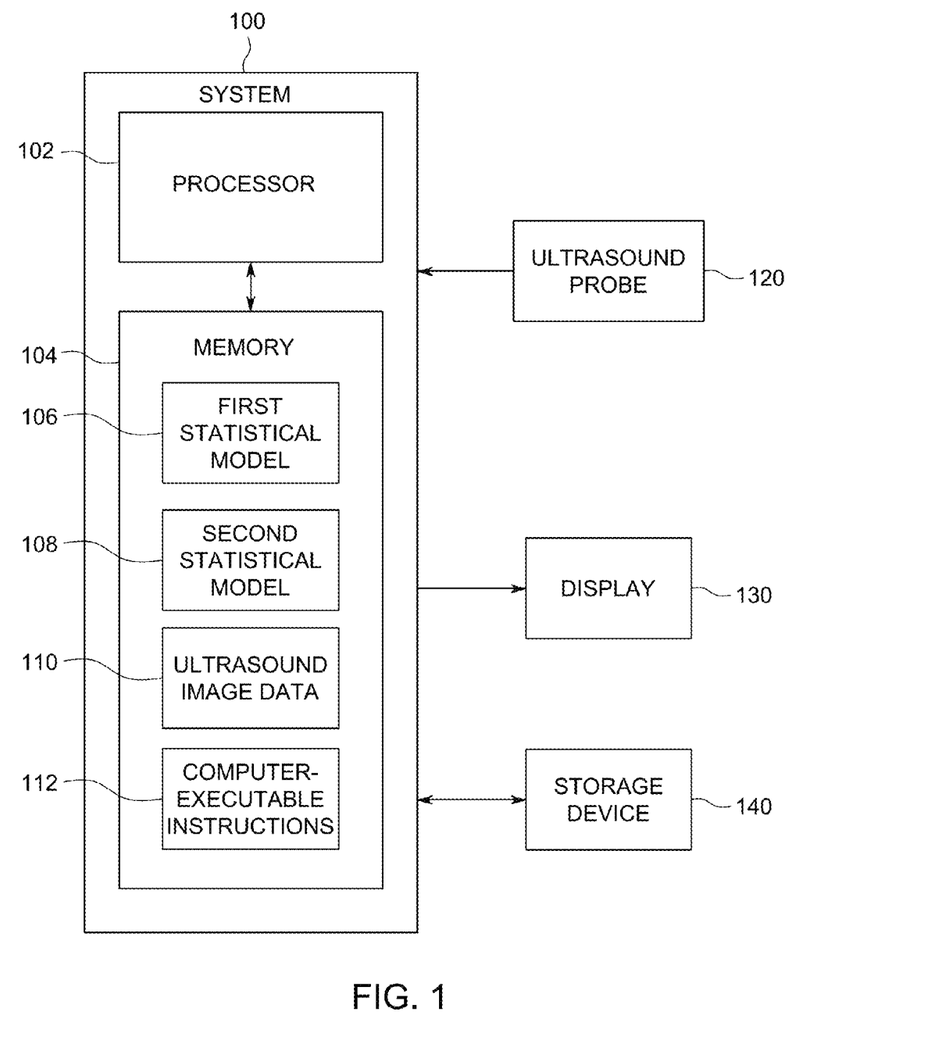
FIG. 1 is a block diagram of an example of a system for analyzing a fetal ultrasound image, in accordance with an embodiment.

FIG. 1 is a block diagram of an example of a system 100 for analyzing a fetal ultrasound image, according to an embodiment. The system 100 includes a computer having a processor 102 and a memory 104 operatively coupled to the processor 102. The memory is configured to store data representing a first statistical model 106 and a second statistical model 108, ultrasound image data 110 representing an ultrasound image, and computer-executable instructions 112 that can be executed by the processor 102 to implement, for example, an abdominal detector. The system 100 may be operatively coupled to an ultrasound probe 120 for receiving the ultrasound image data 110 therefrom, and a display 130 for displaying ultrasound images.

Figure 2A:
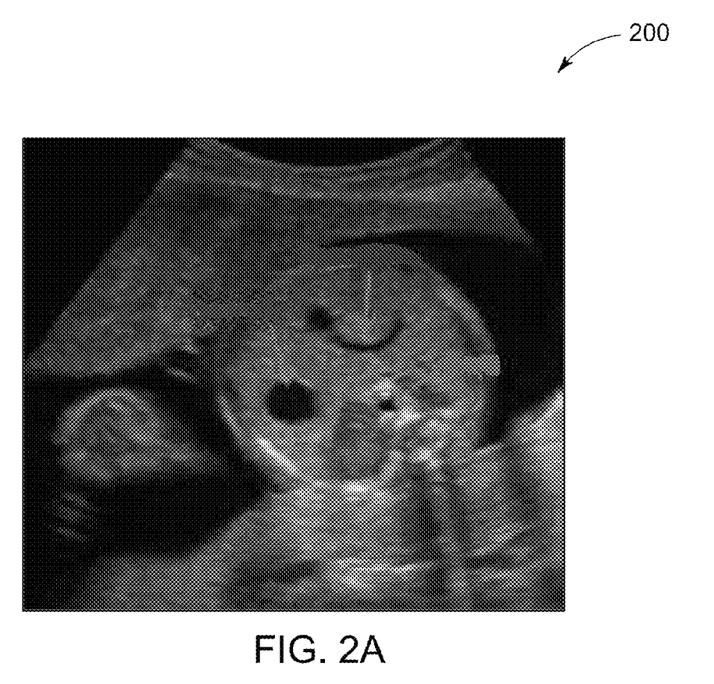
FIG. 2A depicts an example of an ultrasound image of a fetal abdomen.

FIG. 2A is an example of an ultrasound image of a fetal abdomen 200. The ultrasound image is normally viewed as a cross-section of the anatomy being scanned; the cross-section is obtained in the scan plane of the ultrasound image, as will be understood by one of skill in the art. According to some embodiments, it is appreciated that the scan plane of the ultrasound image has, in the context of anatomical measurements, a bearing on measurement accuracy. For instance, the abdominal circumference of the fetus can be measured at the level of the stomach, including the left portal view at the umbilical region, such as shown in FIG. 2A.

Figure 2B:
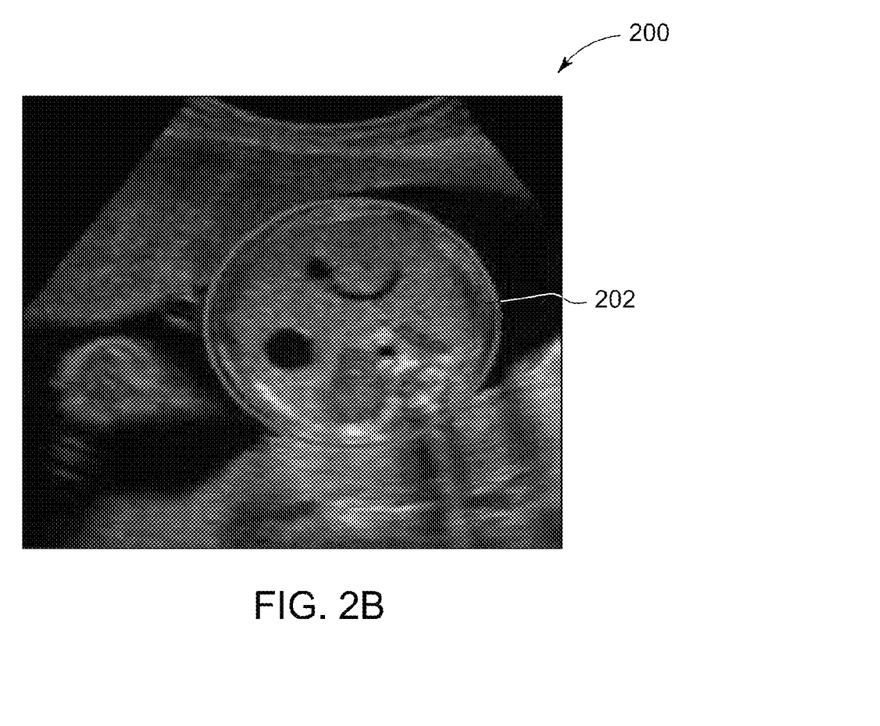
FIG. 2B depicts an example of the ultrasound image of FIG. 2A, showing a contour along the circumference of the fetal abdomen, in accordance with an embodiment.

FIG. 2B shows an example of the ultrasound image 200 of FIG. 2A with a contour 202 superimposed over the image along or near the circumference of the fetal abdomen, according to some embodiments. The contour 202 can be used to measure the abdominal circumference. A good scan plane for measuring the circumference of the abdomen may therefore include the presence of one or more anatomical landmarks, such as the stomach and the portal vein, while other scan planes not including such landmarks may lead to an inaccurate measurement of the fetal abdominal circumference. Therefore, it is desirable to provide the user with guidance for choosing the best scan plane to take measurements of the fetal abdominal circumference. In some embodiments, the guidance includes rating the scan plane based on the presence (or absence) of certain anatomical structures, such as the fetal abdomen, stomach and/or portal vein, in the scan plane.

In some embodiments, the rating can be assigned to the scan plane of the ultrasound image using a classification by detection process. Certain anatomical structures present in the scan plane can be detected and classified according to one or more statistical models obtained from training data, which represents conforming (positive) and/or non-conforming (negative) exemplars of the corresponding anatomical features. Referring again to FIG. 1, this process includes finding a region of interest (ROI) in the ultrasound image represented by the ultrasound image data 110 by training an abdomen detector to generate a statistical model of an abdomen. In an embodiment, the abdomen detector uses the first statistical model 106 to determine whether an object in the scan plane is an abdomen. Once detected, the ROI encompasses the abdomen. Within the ROI, one or more other fetal anatomical structures may be detected. For example, a stomach can be detected based on training data for the stomach, and a portal vein can be detected based on training data for the portal vein. The second statistical model 108 can be used to determine whether an object in the ROI is a stomach and/or portal vein.

The scan plane can be rated based on whether one or more of the fetal anatomical structures are present in the scan plan. The ratings may, for example, include bad, acceptable and good. The rating may be bad if an ROI is not found or if none of the anatomical structures are detected. The rating may be acceptable if one of the anatomical structures is present within the ROI, for example, if either the stomach or the portal vein, but not both, are detected. The rating may be good if all the anatomical features are present in the ROI, for example, if both the stomach and the portal vein are detected. The user may use the rating to determine whether the scan plane is appropriate for making measurements of the fetal abdominal circumference.

Figure 3A:
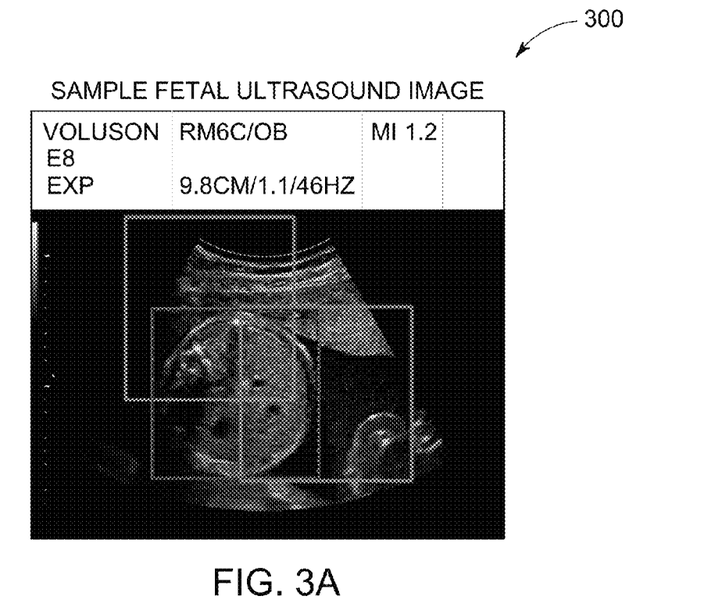
FIG. 3A depicts an example of an ultrasound image of a fetal abdomen.
Figure 3B:
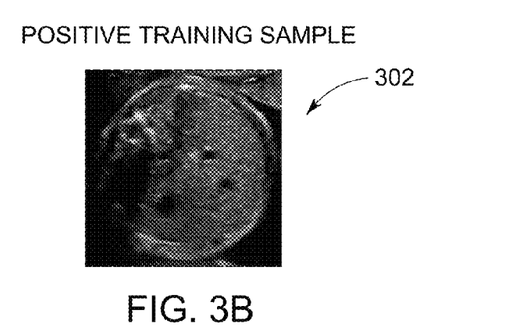
FIG. 3B depicts an example of a positive training sample of the ultrasound image of FIG. 3A, in accordance with an embodiment.
Figure 3C:
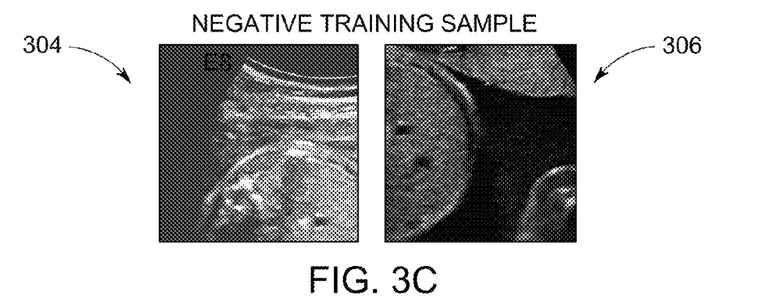
FIG. 3C depicts examples of negative training samples of the ultrasound image of FIG. 3A, in accordance with an embodiment.

As discussed above, in some embodiments, the abdomen detector can be obtained by learning a statistical model representing the abdomen in training images. The statistical model may be learned, for example, by training an AdaBoost classifier. For instance, in some embodiments, 252 clinical abdominal ultrasound images may be used for training the detector. FIG. 3A is an exemplary abdominal ultrasound image 300 that may be used for training the abdomen detector. FIG. 3B shows an example of a positive training sample 302, including a fetal abdomen, and FIG. 3C shows examples of negative training samples 304 and 306, respectively, including only portions of a fetal abdomen, each taken from the sample abdominal ultrasound image 300 of FIG. 3A, respectively.

In an embodiment, 252 positive training samples and thousands of negative training samples can be obtained using different sample abdominal ultrasound images, such as shown in FIG. 3A. In other embodiments, different numbers of positive and/or negative training samples can be used. To obtain a sufficiently large set of training data, affine transformations and random selection of backgrounds can be applied to the positive training samples. In this manner a positive training set of approximately 4,000 samples may be obtained. These transformations may represent anatomically realistic fetal ultrasound images and possible variations that may occur during scan time. For the negative training set, negative training abdomen and non-abdomen ultrasound image samples may be used. The negative training set may be used help to decrease the false positive rate of the training abdomen detector.

Once the training data is obtained, the abdomen detector can be obtained via training the AdaBoost classifier. To find the ROI, the trained abdomen detector scans through the input images and output regions that are classified as abdomen. The detection may be very fast and may process, for example, 20 images per second.

Once the ROI is obtained, the stomach and/or portal vein can be detected in the scan plane if they are present. In some embodiments, the stomach and portal vein detectors are only used within the ROI. The entire process for detecting the abdomen ROI and detecting the stomach and the portal vein within the ROI may take, for example, about 0.07 seconds.

In some embodiments, once an appropriate scan plane including an abdomen, stomach and portal vein is identified, the abdominal circumference can be automatically measured by identifying and measuring a contour that is coincident to the abdominal boundary, for instance, the perimeter of an ellipse encapsulating the abdominal tissue, such as the contour 202 shown in FIG. 2B. To improve the accuracy of the measurement, the fetal abdomen image can be enhanced so as to improve the tissue signature lining the fetal abdomen, which represents the boundary of the abdomen. The fetal-abdomen image may, for example, be enhanced using an adaptive histogram filter to equalize the gray-level distribution across the image and to enhance the soft-tissue contrast.

Prior to enhancement, noise may be reduced or removed from the ultrasound image. One possible source of noise in ultrasound data is multiplicative speckle noise. However, as a result of the log-compression (applied to the data during the scan-conversion process), this noise may be transformed into an additive noise, and is therefore amenable to removal using least-squares techniques. In an embodiment, a 2D wiener filter can be used for noise reduction in the ultrasound image. The filter can be formulated as follows:

$$I_f(x, y) = \mu(x, y) + \frac{\sigma(x, y)^2 \ v(x, y)^2}{\sigma(x, y)^2}(I(x, y) - \mu(x, y)) \quad (1)$$

where I is the input image, $I_f$ is the filtered image, and μ, σ and ν are the local mean, local variance and estimate of the image noise, respectively. μ, σ and ν can be estimated based on the expressions below (where s is the half-kernel width and is set to 2):

$$\mu(x, y) = \frac{1}{s^2}\sum_{x-s}^{x+s}\sum_{y-s}^{y+s} I(x, y), \sigma(x, y) = \frac{1}{s^2}\sum_{x-s}^{x+s}\sum_{y-s}^{y+s} (I(x, y) - \mu)^2, \quad (2)$$

$$v(x, y) = \max[\sigma(x, y), \mathrm{mean}(\sigma)]$$

Subsequent to wiener filtering, the image can be subjected to coherence enhancement. While the tissue lining the abdomen is a continuous and coherent entity, it often appears disjointed in ultrasound images owing to several factors some of which could be related to tissue alignment (tissue scatters ultrasound beam away from the probe) and tissue occlusion. It is therefore possible, in the context of abdominal circumference measurement, to employ a filter that is able to smooth across these spatial discontinuities while preserving the contrast between the tissue and its surrounding background.

In some embodiments, a coherence enhancing diffusion filter can be used to smooth across the spatial discontinuities in the scan plane. In the first step, the structure tensor $J_p$ corresponding to the input image I can be computed using the expressions below:

$$U_\sigma(x,y) = (K_\sigma \otimes I)(x,y)$$

$$J_p(\nabla U_\sigma) = K_\rho \otimes (\nabla U_\sigma + \nabla U_\sigma^T) \quad (3)$$

In equation 3, $K_\sigma(\sigma=10)$ and $K_\rho(\rho=31)$ are Gaussian smoothing kernels and ∇ is the gradient operator. The non-principal eigenvector (i.e., the eigenvector corresponding to smaller of the two eigenvalues) of the structure tensor is aligned perpendicular to the gradient direction and is therefore potentially indicative of the orientation of the underlying anatomy. The structure tensor is also closely tied to the notion of coherence, where the parameter κ signifies the presence (κ~large) or absence (κ~0) of an underlying coherent structure.

$$\kappa = (\mu_1 - \mu_2)^2 \quad (4)$$

In equation 4, $\mu_1$ and $\mu_2$ are the eigenvalues of the structure tensor. The value of κ is likely to be high in regions where the abdominal tissue is present as this tissue appears as a band-like structure and possesses a high degree of coherence. Once the coherence at each point in the image is determined (eq. (4)) the image can be smoothed based on the diffusion formulation below:

$$\frac{\partial I}{\partial s} = \mathrm{div}(D \nabla I) \quad (5)$$

D is the diffusion tensor and has the same eigenvectors as $J_p$, and its eigenvalues are given by:

$$\lambda_1 = \alpha, \quad \lambda_2 = \alpha + (1 - \alpha)\exp\left(\frac{-C}{k}\right) \quad (6)$$

In equation 6, α (=0.001) is a small constant and C (=1) serves as a threshold parameter. When k>>C, $\lambda_2$ tends to 1, and therefore the smoothing is performed along the eigenvector parallel to the anatomical orientation. This enhances the abdominal tissue connectivity while maintaining the contrast between the tissue and the surrounding region.

In some embodiments, the coherence enhanced image can be transformed into multiple binary representations, where the image pixels corresponding to the abdominal tissue are highlighted in each of these representations. Multiple binary representations impose a certain degree of redundancy, which helps ensure that parts of the abdominal tissue appear in at least one or more of the binary images. The multiple binary representations may be generated by computing the likelihood of an ultrasound image to contain vessel- or ridge-like structures.

In the first step of transforming the coherence enhanced image into multiple binary representations, the enhanced image can be convolved with a series of Gaussian second derivative filters, and the responses at each image pixel can be stacked into a [2*2] matrix to obtain the Hessian:

$$D_{xx} = H_{xx} \otimes I, D_{yy} = H_{yy} \otimes I, D_{xy} = H_{xy} \otimes I, \quad (7)$$

$$D = \begin{bmatrix} D_{xx} & D_{xy} \\ D_{xy} & D_{yy} \end{bmatrix}$$

where I is the input image, $H_{xx}$, $H_{yy}$ and $H_{xy}$ are the second derivative Gaussian filters, ⊗ is the convolution operation, and D is the hessian matrix formed by stacking the filter outputs $D_{xx}$, $D_{yy}$ and $D_{xy}$ at each image pixel. The ratio of eigenvalues of the matrix D ($\lambda_1$, $\lambda_2$) is a measure of the isotropy (anisotropy) of the underlying structure. A small ratio is indicative of a ridge-like feature that possesses a definitive orientation and therefore exhibits strong anisotropy. This anisotropy can be emphasized by embedding the ratio of the eigenvalues into a functional form as expressed below:

$$I_f = \exp\left(-\left(\frac{\lambda_2}{\lambda_1}\right)^2 / \beta\right)\left(1 - \exp\left(\frac{(\lambda_1^2 + \lambda_2^2)}{c}\right)\right), \text{ where } \lambda_2 < \lambda_1 \quad (8)$$

where $I_f$ is the filtered output and β(=1) and c (=450) are constants. The filtered output varies in the range [0, 1] with values near one indicating a strong presence of a ridge-like structure. Since the anatomical structure may manifest itself at different scales, the proposed algorithm may be repeated at multiple scales (e.g., the number of scales=8), and the maximum output (from all the scales) at each pixel can be stored as the final output. The output may, for example, be binarized by selecting a simple threshold of 0.5.

As discussed above, the abdominal tissue may have a ridge-like appearance, and therefore may have a high degree of curvature. The local (pixel-wise) curvature can be estimated from the enhanced image based on the below expression:

$$I_c = \frac{\nabla \cdot \left(\frac{\partial I}{\partial x}\hat{x} + \frac{\partial I}{\partial y}\hat{y}\right)}{\sqrt{\left(\frac{\partial I}{\partial x}\right)^2 + \left(\frac{\partial I}{\partial y}\right)^2}} \quad (9)$$

where I is the input image (coherence enhanced image) and $I_c$ is the image obtained at the end of the curvature transform.

The image $I_c$ can be binarized by selecting a threshold based on the simple k-means procedure (e.g., the number of levels=5, threshold level=2).

Sometimes parts of the fetal abdomen are in proximity to the amniotic fluid, and therefore one way to segment the abdominal tissue is to segment the fluid-tissue interface in the ultrasound image. Amniotic fluid appears anechoic in the ultrasound image, and therefore can be segmented by using a simple intensity thresholding procedure (e.g., a K-means procedure). Once the amniotic fluid regions are determined, the fluid tissue interface can be identified by projecting rays from the top and bottom of the image and enumerating points at which these rays pass through this interface (fluid to tissue).

Some embodiments disclosed herein transform the coherence enhanced image into multiple binary images, where each binary image contains whole or parts of the abdominal tissue (e.g., pixels where abdominal tissue is present are set to one). Quite often, however, the abdominal tissue does not appear as a distinct entity but is instead connected to neighboring structures or noise artifacts. The noise artifacts may appear either as distinct regions or be attached to the abdominal contour itself. As described herein, any region that is attached to the region of interest (e.g., an abdominal contour) is referred to as an artifact.

It should be understood that embodiments disclosed herein for artifact elimination are demonstrated on the upper abdominal contour, but may be extended to any other region/contour without loss of generality. One process for artifact elimination/contour pruning, according to some embodiments, is described below.

In the first step, the binary region can be skeletonized to yield a connected region, which has an average thickness of one pixel. This connected region can be efficiently represented as a graph structure where pixels having more than two neighbors constitute a branching node (e.g., neighbors refers to the pixels in an eight connected neighborhood, around the pixel under consideration, that have a value of one); pixels having exactly one neighbor constitute a terminal node and all other pixels (e.g., having exactly two neighbors) constitute a branch.

Performing the first step helps ensure that the artifact is almost always connected to the contour of interest through a branching node. While each branching node may be attached to three or more branches, it is rare that two artifactual structures are attached to the abdominal contour at exactly the same point, and therefore it may be assumed that any branching node is attached exactly to three distinct branches only.

In the next step, at each branching node, a quadratic fit can be performed between all pairs of branches, and the fit that yields the least residual error is identified. The branches corresponding to the least residual error can be merged together as a single branch and the remaining branch can be separated from the merged structure. In computing the quadratic residual error, cognizance is taken of the fact as to whether the quadratic fit results in a convex or concave structure. If the resulting structure is convex, then it is appended to a convex set; otherwise it is appended to a concave set. It is noted that at any branching node, the branch that does not get merged is not discarded but rather appended to one of two sets (e.g., concave or convex) as a separate entity.

In the next step, since there is no prior knowledge on which of the binary candidate regions belong to the abdominal contour, a pruning process can be applied to all the candidate regions from all the binary images, and the corresponding output can be stored in the convex or concave index set. The contour co-ordinates for each of the candidates may, for example, be stored as a vector sequence.

In some embodiments, one objective of candidate contour selection is to select one candidate each from the convex and concave sets so as to obtain a reasonable representation of the tissue lining the abdominal circumference. In the first step, one candidate contour each from the concave and convex set is selected, and an ellipse fit is performed on the co-ordinate pairs representing these contours. Every possible pair of candidate contours (one from convex and one from concave) can be examined, and the parameters resulting from this combination are assigned to a set as follows:

$$\epsilon_{ij} = [Y_r, X_r, y_c, x_c, a, b], \forall i \in \text{convex} \ \& \ j \in \text{concave}$$

where $Y_r$ is the set of y co-ordinates of all pixels belonging to the candidate contours; $X_r$ is the set of x co-ordinates of all pixels belonging to the candidate contours; $y_c$ is the y co-ordinate of the fitted ellipse; is the x co-ordinate of the fitted ellipse; a is the major axis length of the fitted ellipse; and b is the minor axis length of the fitted ellipse.

In the next step, a candidate i can be selected from the convex set and a candidate j can be selected from the concave set such that the parameter set defined by $\epsilon_{ij}$ is most likely to originate from candidate contours belonging to the abdominal boundary. This candidate set can be chosen by evaluating certain metrics of abdominal anatomic manifestation and selecting the candidate set that maximizes a normalized score over all the metrics. The metrics, which are largely a function of $\epsilon_{ij}$, may, for example, include eccentricity, ellipse fit regression error, elliptical circumference, orientation, location, etc.

Once the candidate contour set (i, j) is identified, the elliptical fit can be superposed on the original image to obtain a coarse outline of the abdominal contour. This contour may be used to measure the circumference of the fetal abdomen.

In some embodiments, the ellipse shown, for example, may be slightly underestimated with respect to the true abdominal boundary. An indication as to the true edge of the abdominal boundary includes the presence of amniotic fluid surrounding the fetal abdomen. Therefore, to capture the true abdominal boundary, the amniotic fluid surrounding the abdomen can be detected, and the elliptical boundary can be adjusted so as to glaze the fluid boundary.

Figure 4:
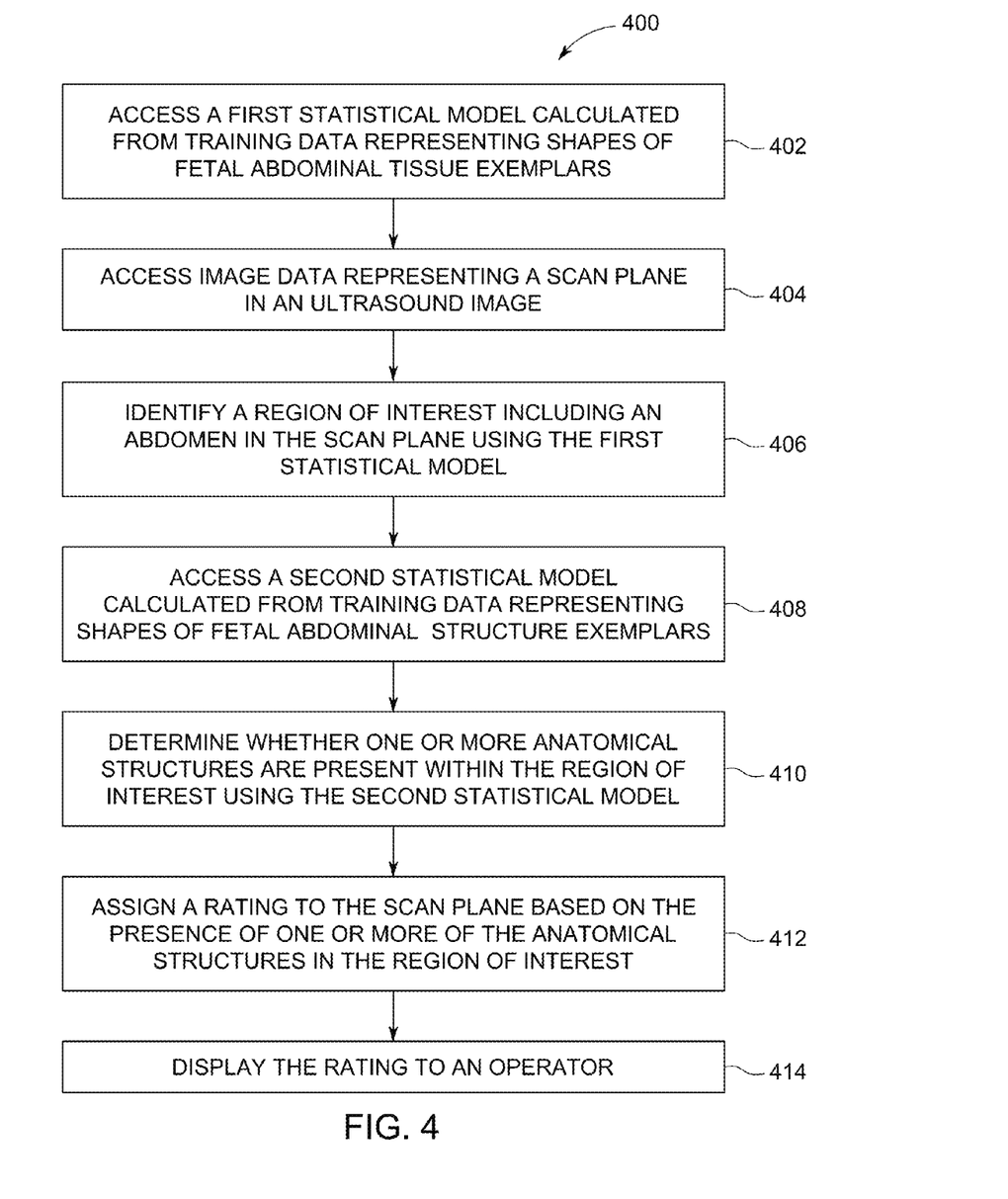
FIG. 4 is a flow diagram of an example of a process for analyzing a fetal ultrasound image, in accordance with an embodiment.

FIG. 4 is a flow diagram of an example of a process 400 for analyzing a fetal ultrasound image, according to an embodiment. Process 400 generally includes identifying an region of interest in a scan plane of an ultrasound image including an abdomen, identifying one or more anatomical structures in the scan plane based on training data, and assigning a rating to the scan plane based on the presence or absence of one or more of the identified anatomical structures in the scan plane.

At step 402, a first statistical model (e.g., the first statistical model 106 of FIG. 1), which may be calculated from training data representing shapes of conforming and/or non-conforming, or positive and/or negative, fetal abdominal tissue exemplars, is accessed, e.g., by the processor 102. At step 404, ultrasound image data (e.g., the ultrasound image data 110 of FIG. 1), which represents a scan plane in an ultrasound image, is accessed, e.g., by the processor 102. At step 406, a region of interest, including an abdomen in the scan plane, is identified using the first statistical model.

At step 408, once the region of interest has been identified, a second statistical model (e.g., the second statistical model 108 of FIG. 1), which is calculated from training data representing shapes of conforming and/or non-conforming, or positive and/or negative, fetal anatomical structure exemplars (e.g., stomach and/or portal vein), is accessed, e.g., by the processor 102. At step 410, based on the region of interest, it is determined whether one or more anatomical structures are present within the region of interest using the second statistical model. At step 412, a rating is assigned to the scan plane based on the presence of one or more of the anatomical structures in the region of interest. For example, the rating may be good if both the stomach and the portal vein are present in the scan plane; acceptable if either the stomach or the portal vein are present, and bad otherwise (i.e., neither the stomach nor the portal vein are present in the scan plane). In some embodiments, at step 414, the rating is displayed to an operator, for example, via the display 130 of FIG. 1. Computer-executable instructions (e.g., the computer-executable instructions 112 of FIG. 1) may, for example, be executed by a processor (e.g., the processor 102) to perform steps 402-414 in accordance with one or more embodiments described herein.

Figure 5:
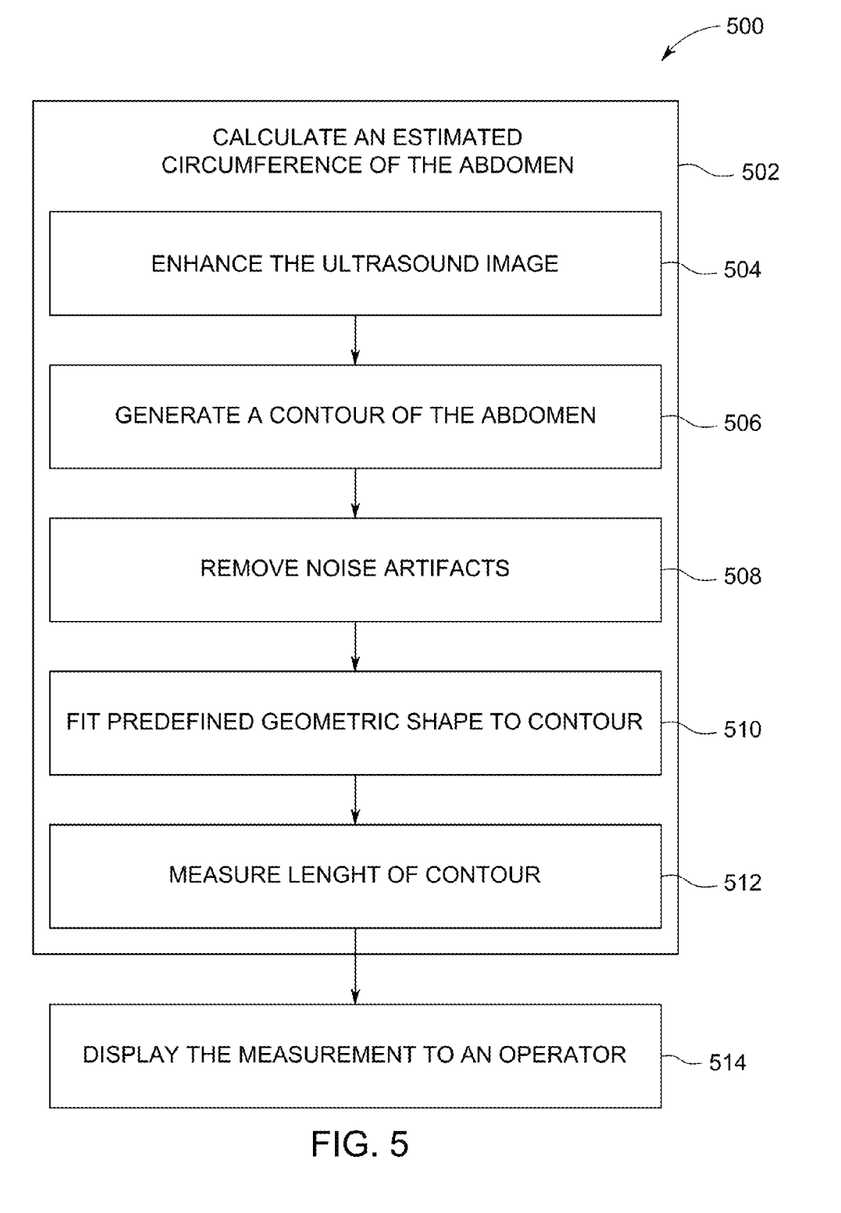
FIG. 5 is a flow diagram of an example of a process for analyzing a fetal ultrasound image, in accordance with an embodiment.

FIG. 5 is a flow diagram of an example of a process 500 for analyzing a fetal ultrasound image, according to an embodiment. Process 500 generally includes calculating an estimated circumference of the fetal abdomen by generating a contour of the abdomen in the enhanced ultrasound image, and estimating the abdominal circumference based on the length of the contour.

At step 502, an estimated circumference of the abdomen is calculated within, for example, the region of interest identified in step 406 of process 400. As one example, step 502 may include one or more of the following steps. At step 504, the ultrasound image can be enhanced using a filter so as to increase a contrast between the abdomen and other anatomical structures in the scan plane. At step 506, a contour of the abdomen can generated. At step 508, any noise artifacts in the scan plane, e.g., noise artifacts adjacent to the abdomen, can be removed. At step 510, a predefined geometric shape can be fitted to the contour. At step 512, the estimated circumference of the abdomen can be calculated by measuring the length of the contour (e.g., the length of the predefined geometric shape). In some embodiments, at step 514, the measurement is displayed to the operator, for example, via the display 130 of FIG. 1. Computer-executable instructions (e.g., the computer-executable instructions 112 of FIG. 1) may, for example, be executed by a processor (e.g., the processor 102) to perform steps 502-514 in accordance with one or more embodiments described herein.

Systems and methods disclosed herein may include one or more programmable processing units having associated therewith executable instructions held on one or more non-transitory computer readable medium, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process.

Displays and/or other feedback components may also be included, for example, for rendering a graphical user interface, according to the present disclosure. The display and/or other feedback components may be stand-alone equipment or may be included as one or more components/modules of the processing unit(s). In exemplary embodiments, the display and/or other feedback components may be used to simultaneously describe both morphological and statistical representations of a field-of-view of an ultrasound image.

The actual software code or control hardware which may be used to implement some of the present embodiments is not intended to limit the scope of such embodiments. For example, certain aspects of the embodiments described herein may be implemented in code using any suitable programming language type such as, for example, assembly code, C, C# or C++ using, for example, conventional or object-oriented programming techniques. Such code is stored or held on any type of suitable non-transitory computer-readable medium or media such as, for example, a magnetic or optical storage medium.

As used herein, a "processor," "processing unit," "computer" or "computer system" may be, for example, a wireless or wire line variety of a microcomputer, minicomputer, server, mainframe, laptop, personal data assistant (PDA), wireless e-mail device (for example, "BlackBerry," "Android" or "Apple," trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include non-transitory storage medium for storing software, including a hard disk, an optical disk, floppy disk, ROM (read only memory), RAM (random access memory), PROM (programmable ROM), EEPROM (electrically erasable PROM), flash memory storage devices, or the like.

The system 100 of FIG. 1 may be any computer system, such as a workstation, desktop computer, server, laptop, handheld computer, tablet computer (e.g., the iPad® tablet computer), mobile computing or communication device (e.g., the iPhone® mobile communication device, the Android® mobile communication device, and the like), or other form of computing or telecommunications device that is capable of communication and that has sufficient processor power and memory capacity to perform the operations described herein. In exemplary embodiments, a distributed computational system may be provided including a plurality of such computing devices.

The system 100 may include one or more non-transitory computer-readable media having encoded thereon one or more computer-executable instructions or software for implementing the exemplary methods described herein. The non-transitory computer-readable media may include, but are not limited to, one or more types of hardware memory and other tangible media (for example, one or more magnetic storage disks, one or more optical disks, one or more USB flash drives), and the like. For example, the memory 104 included in the system 100 may store computer-readable and computer-executable instructions or software for implementing a graphical user interface as described herein. The processor 102, and in some embodiments, one or more additional processor(s) and associated core(s) (for example, in the case of computer systems having multiple processors/cores), are configured to execute computer-readable and computer-executable instructions or software stored in the memory 104 and other programs for controlling system hardware. Processor 102 may be a single core processor or a multiple core processor.

The memory 104 may include a computer system memory or random access memory, such as DRAM, SRAM, EDO RAM, and the like. The memory 104 may include other types of memory as well, or combinations thereof.

A user may interact with the system 100 through the display 130, which may display ultrasound images and other information in accordance with exemplary embodiments described herein. The display 130 may also display other aspects, elements and/or information or data associated with exemplary embodiments. The system 100 may include other I/O devices for receiving input from a user, for example, a keyboard or any suitable multi-point touch interface, a pointing device (e.g., a mouse, a user's finger interfacing directly with a display device, etc.). The system 100 may include other suitable conventional I/O peripherals.

The system 100 may include one or more storage devices 140, such as a durable disk storage (which may include any suitable optical or magnetic durable storage device, e.g., RAM, ROM, Flash, USB drive, or other semiconductor-based storage medium), a hard-drive, CD-ROM, or other computer readable media, for storing data and computer-readable instructions and/or software that implement exemplary embodiments as taught herein. In exemplary embodiments, the one or more storage devices 140 may provide storage for data that may be generated by the systems and methods of the present disclosure. For example, storage device 140 may provide storage for image data and/or storage for data analysis (e.g., storage for results of parameters for any of the image or statistical analyses described herein such as image segmentation results). The one or more storage devices 140 may further provide storage for computer readable instructions relating to one or more processes as described herein. The one or more storage devices 140 may be provided on the system 100 and/or provided separately or remotely from the system 100.

The system 100 may run any operating system, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system may be run in native mode or emulated mode. In an exemplary embodiment, the operating system may be run on one or more cloud machine instances.

Having thus described several exemplary embodiments of the invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A computer-implemented method for analyzing a fetal ultrasound image, the computer including a processor and a memory operatively coupled to the processor, the method comprising:
   accessing, in the memory, a first statistical model calculated from training data representing shapes of conforming fetal abdominal tissue exemplars;
   accessing, in the memory, image data representing a scan plane in an ultrasound image;
   identifying, by the processor, a region of interest including an abdomen in the scan plane using the first statistical model;
   accessing, in the memory, a second statistical model calculated from training data representing shapes of conforming fetal anatomical structure exemplars;
   determining, by the processor, whether one or more anatomical structures are present within the region of interest using the second statistical model; and
   assigning, by the processor, a rating to the scan plane based on the presence of the one or more anatomical structures in the region of interest.

2. The computer-implemented method of claim 1, wherein the one or more anatomical structures include at least one of a stomach and a portal vein.

3. The computer-implemented method of claim 2, further comprising assigning the rating to be one of:
   good, if both the stomach and the portal vein are present in the scan plane,
   acceptable, if either the stomach or the portal vein is present in the scan plane; and
   bad, otherwise.

4. The computer-implemented method of claim 3, further comprising displaying, by the processor via an operator display operatively coupled to the processor, the rating and the region of interest.

5. The computer-implemented method of claim 1, further comprising calculating, by the processor, an estimated circumference of the abdomen.

6. The computer-implemented method of claim 5, further comprising enhancing, by the processor, the ultrasound image using a filter so as to increase a contrast between the abdomen and other anatomical structures present in the scan plane.

7. The computer-implemented method of claim 6, wherein calculating the estimated circumference comprises:
   generating, by the processor, a contour of the abdomen, wherein the contour is coincident to a boundary between the abdomen and the other anatomical structures present in the scan plane; and
   measuring a length of the contour.

8. The computer-implemented method of claim 7, further comprising removing, by the processor, noise artifacts adjacent to the contour.

9. The computer-implemented method of claim 8, further comprising fitting a predefined geometric shape to the contour.

10. A non-transitory computer-readable medium having stored thereon computer-executable instructions that when executed by a computer cause the computer to:
    access a first statistical model calculated from training data representing shapes of conforming fetal abdominal tissue exemplars;
    access image data representing a scan plane in an ultrasound image;
    identify a region of interest including an abdomen in the scan plane using the first statistical model;
    access a second statistical model calculated from training data representing shapes of conforming fetal anatomical structure exemplars;
    determine whether one or more anatomical structures are present within the region of interest using the second statistical model; and
    assign a rating to the scan plane based on the presence of the one or more anatomical structures in the region of interest.

11. The computer-readable medium of claim 10, wherein the one or more anatomical structures include at least one of a stomach and a portal vein.

12. The computer-readable medium of claim 11, further comprising computer-executable instructions that when executed by the computer cause the computer to assign the rating to be one of:
    good, if both the stomach and the portal vein are present in the scan plane,
    acceptable, if either the stomach or the portal vein is present in the scan plane; and
    bad, otherwise.

13. The computer-readable medium of claim 12, further comprising computer-executable instructions that when executed by the computer cause the computer to display, via an operator display, the rating and the region of interest.

14. The computer-readable medium of claim 10, further comprising computer-executable instructions that when executed by the computer cause the computer to calculate an estimated circumference of the abdomen.

15. The computer-readable medium of claim 14, further comprising computer-executable instructions that when executed by the computer cause the computer to enhance the ultrasound image using a filter so as to increase a contrast between the abdomen and other anatomical structures present in the scan plane.

16. The computer-readable medium of claim 15, further comprising computer-executable instructions that when executed by the computer cause the computer to:
generate a contour of the abdomen, wherein the contour is coincident to a boundary between the abdomen and the other anatomical structures in the scan plane; and
measure a length of the contour.

17. The computer-readable medium of claim 16, further comprising computer-executable instructions that when executed by the computer cause the computer to remove noise artifacts adjacent to the contour.

18. The computer-readable medium of claim 17, further comprising computer-executable instructions that when executed by the computer cause the computer to fit a predefined geometric shape to the contour.

19. A system for analyzing a fetal abdominal ultrasound image, the system comprising:
a processor;
an input operatively coupled to the processor and configured to receive image data representing a scan plane in an ultrasound image; and
a memory operatively coupled to the processor, the memory including computer-executable instructions that when executed by the processor cause the processor to:
access a first statistical model calculated from training data representing shapes of conforming fetal abdominal tissue exemplars;
access the image data;
identify a region of interest including an abdomen in the scan plane using the first statistical model;
access a second statistical model calculated from training data representing shapes of conforming fetal anatomical structure exemplars;
determine whether one or more anatomical structures are present within the region of interest using the second statistical model; and
assign a rating to the scan plane based on the presence of the one or more anatomical structures in the region of interest.

20. The system of claim 19, wherein the one or more anatomical structures include at least one of a stomach and a portal vein.

21. The system of claim 20, wherein the memory further includes computer-executable instructions that when executed by the processor cause the processor to assign the rating to be one of:
good, if both the stomach and the portal vein are present in the scan plane, acceptable, if either the stomach or the portal vein is present in the scan plane; and
bad, otherwise.

22. The system of claim 21, wherein the memory further includes computer-executable instructions that when executed by the processor cause the processor to display, via an operator display, the rating and the region of interest.

23. The system of claim 19, wherein the memory further includes computer-executable instructions that when executed by the processor cause the processor to calculate an estimated circumference of the abdomen.

24. The system of claim 23, wherein the memory further includes computer-executable instructions that when executed by the processor cause the processor to enhance the ultrasound image using a filter so as to increase a contrast between the abdomen and other anatomical structures present in the scan plane.

25. The system of claim 24, wherein the memory further includes computer-executable instructions that when executed by the processor cause the processor to:
generate a contour of the abdomen, wherein the contour is coincident to a boundary between the abdomen and the other anatomical structures in the scan plane; and
measure a length of the contour.

26. The system of claim 25, wherein the memory further includes computer-executable instructions that when executed by the processor cause the processor to remove noise artifacts adjacent to the contour.

27. The system of claim 26, wherein the memory further includes computer-executable instructions that when executed by the processor cause the processor to fit a predefined geometric shape to the contour.

* * * * *

UNITED STATES PATENT AND TRADEMARK OFFICE
CERTIFICATE OF CORRECTION

Page 1 of 1

PATENT NO.         : 8,831,311 B2
APPLICATION NO.    : 13/731140
DATED              : September 9, 2014
INVENTOR(S)        : Swamy et al.

It is certified that error appears in the above-identified patent and that said Letters Patent is hereby corrected as shown below:

In the Specification

In Column 10, Line 16, delete "is the" and insert -- $x_c$ is the --, therefor.

Signed and Sealed this
Eighteenth Day of November, 2014

Michelle K. Lee
*Deputy Director of the United States Patent and Trademark Office*